(12) United States Patent
Butler

(10) Patent No.: US 8,178,738 B2
(45) Date of Patent: *May 15, 2012

(54) METHOD FOR EXTENDING CATALYST LIFE IN PROCESSES FOR PREPARING VINYL AROMATIC HYDROCARBONS

(75) Inventor: James Butler, League City, TX (US)

(73) Assignee: Fina Technology, Inc., Houston, TX (US)

( * ) Notice: Subject to any disclaimer, the term of this patent is extended or adjusted under 35 U.S.C. 154(b) by 515 days.

This patent is subject to a terminal disclaimer.

(21) Appl. No.: 12/391,063

(22) Filed: Feb. 23, 2009

(65) Prior Publication Data

US 2009/0156873 A1 Jun. 18, 2009

Related U.S. Application Data

(63) Continuation-in-part of application No. 11/145,345, filed on Jun. 3, 2005, now abandoned, which is a continuation-in-part of application No. 10/235,279, filed on Sep. 5, 2002, now Pat. No. 6,936,743.

(51) Int. Cl.
*C07C 5/333* (2006.01)

(52) U.S. Cl. .............. 585/440; 585/441; 585/444
(58) Field of Classification Search ............ 585/440, 585/441, 444

See application file for complete search history.

(56) References Cited

U.S. PATENT DOCUMENTS

| | | | | |
|---|---|---|---|---|
| 4,590,324 A | * | 5/1986 | Satek | 585/444 |
| 5,689,027 A | * | 11/1997 | Abichandani et al. | 585/481 |
| 5,739,071 A | * | 4/1998 | Chen et al. | 502/53 |

* cited by examiner

*Primary Examiner* — Thuan Dinh Dang

(57) ABSTRACT

Methods and systems for extending the life of a dehydrogenation catalyst are described herein. For example, one embodiment includes providing an alkyl aromatic hydrocarbon feed stream to a reaction chamber, contacting the feed stream with a dehydrogenation catalyst to form a vinyl aromatic hydrocarbon, the dehydrogenation catalyst including iron oxide and an alkali metal catalysis promoter and supplying a catalyst life extender to at least one reaction chamber, the reaction chamber loaded with the dehydrogenation catalyst, wherein the catalyst life extender includes a potassium salt of a carboxylic acid.

8 Claims, 2 Drawing Sheets

METHOD FOR EXTENDING CATALYST LIFE IN PROCESSES FOR PREPARING VINYL AROMATIC HYDROCARBONS

CROSS-REFERENCE TO RELATED APPLICATIONS

This application claims the benefit of U.S. patent application Ser. No. 11/145,345, filed Jun. 3, 2005, which claims priority to U.S. patent application Ser. No. 10/235,279, filed on Sep. 5, 2002.

FIELD

Embodiments of the present invention generally relate to aqueous salt addition to high temperature processes.

BACKGROUND

Catalytic dehydrogenation processes generally include the conversion of a paraffin alkylaromatic to the corresponding olefin in the presence of a dehydrogenation catalyst. During such dehydrogenation processes, it is desirable to maintain both high levels of conversion and high levels of selectivity. Unfortunately, dehydrogenation catalysts tend to lose activity when exposed to reaction environments, thereby reducing the level of conversion and/or the level of selectivity. Such losses may result in an undesirable loss of process efficiency. Various methods for catalyst regeneration exist, but such methods generally involve stopping the reaction process and in some cases, removing the catalyst for external regeneration, resulting in increased costs, such as costs related to heat loss and lost production.

One regeneration method includes the addition of a catalyst life extender to the dehydrogenation process. Such processes may avoid/delay the need for catalyst removal from the reaction vessel for regeneration and/or disposal. Unfortunately, such processes generally have required costly implementation systems to avoid system problems, such as fouling and plugging of the process lines.

Therefore, it is desirable to overcome catalyst degradation, while at the same time ensuring that such methods of overcoming the degradation do not result in costly implementation systems, fouling and/or plugging.

SUMMARY

Embodiments of the invention generally include a method for preparing a vinyl aromatic hydrocarbon. The method generally includes providing an alkyl aromatic hydrocarbon feed stream to a reaction chamber, contacting the feed stream with a dehydrogenation catalyst to form a vinyl aromatic hydrocarbon, the dehydrogenation catalyst including iron oxide and an alkali metal catalysis promoter and supplying a catalyst life extender to at least one reaction chamber, the reaction chamber loaded with the dehydrogenation catalyst, wherein the catalyst life extender includes a potassium salt of a carboxylic acid.

DETAILED DESCRIPTION

Introduction and Definitions

A detailed description will now be provided. Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions, when the information in this patent is combined with available information and technology. Various terms as used herein are shown below. To the extent a term used in a claim is not defined below, it should be given the broadest definition persons in the pertinent art have given that term as reflected in printed publications and issued patents at the time of filing.

As used herein, the term "conversion" means the percentage of paraffins or alkylaromatic hydrocarbon transformed.

The term "selectivity" means percentage of alkylaromatic hydrocarbon transformed to the desired product.

The term "activity" refers to the weight of product produced per weight of the catalyst used in the dehydrogenation process per hour of reaction at a standard set of conditions (e.g., grams product/gram catalyst/hr).

The term "loaded" refers to introduction of a catalyst within a reaction vessel.

As used herein, the term "alkali metal" includes but is not limited to, potassium, sodium, lithium and other members of the group IA and IIA metals of the periodic table, such as rubidium and cesium. In the conversion of ethylbenzene to styrene, the alkali metal is generally potassium, but depends upon the alkali metal present in the dehydrogenation catalyst.

As used herein, the term "regeneration" means a process for renewing catalyst activity and/or making the catalyst reusable after its activity has reached an unacceptable level. Examples of such regeneration may include passing steam over the catalyst bed or burning off carbon residue.

Figure 1:
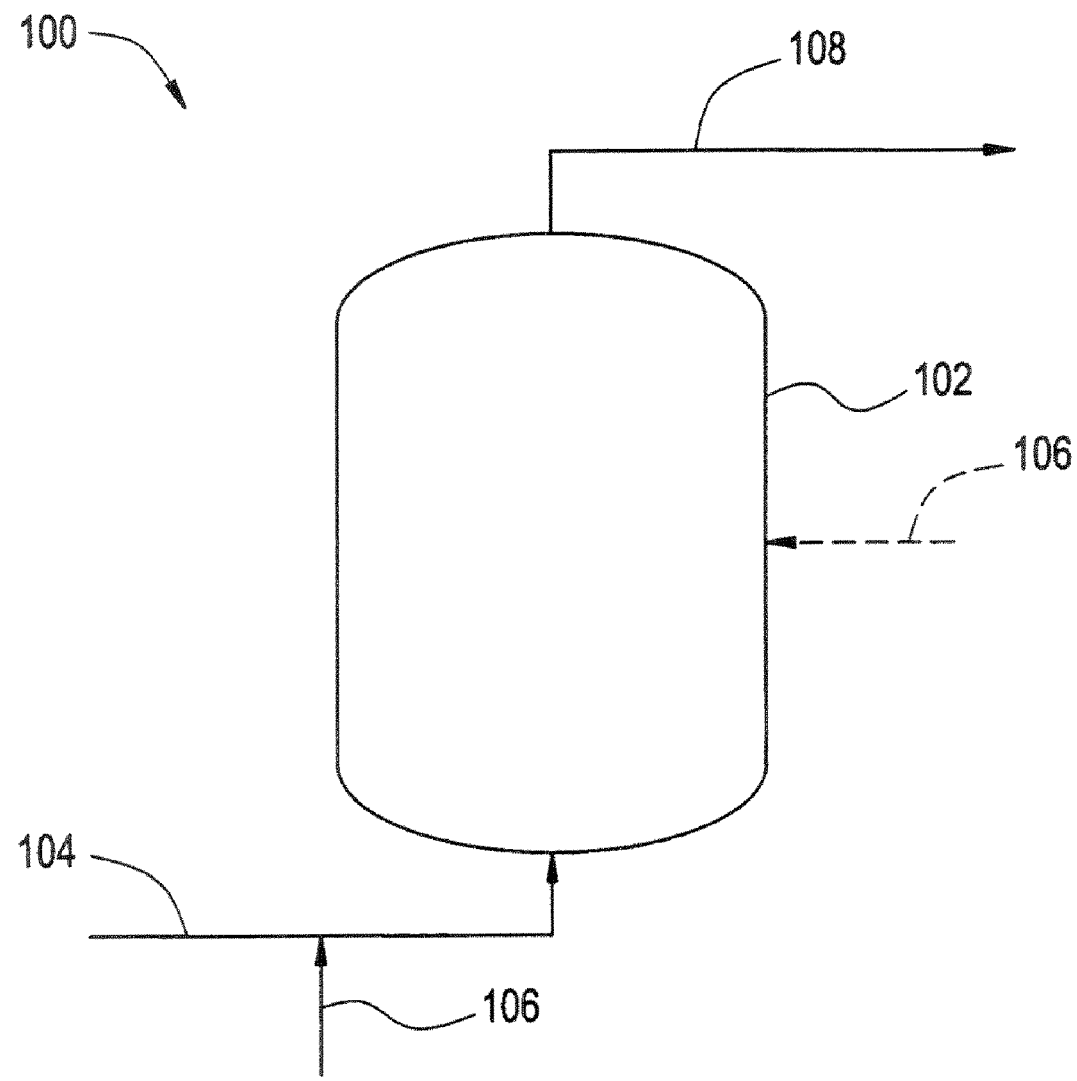
FIG. 1 illustrates a catalytic dehydrogenation system.

FIG. 1 illustrates a catalytic dehydrogenation system 100 including at least one reaction vessel 102 loaded with a dehydrogenation catalyst (not shown). An alkyl aromatic hydrocarbon (AAH) feedstream 104 enters the reaction vessel 102 and contacts the dehydrogenation catalyst to form a vinyl aromatic hydrocarbon (VAH) exit stream 108. Although the process is described here in terms of an alkyl aromatic hydrocarbon feedstream and a vinyl aromatic hydrocarbon exit stream, it is within embodiments of the invention described herein that the feedstream may be and/or include other compounds that may be contacted with a dehydrogenation catalyst to form a product, such as propane (converted to propylene) or butylene (converted to butadiene.) It is further contemplated that the embodiments described herein, such as the supply system described further below, may be used for high temperature processes not utilizing dehydrogenation catalysts, but in need of aqueous injection into the feedstream.

One example of a catalytic dehydrogenation process includes dehydrogenating alkyl aromatic hydrocarbons over a solid catalyst component in the presence of steam (not shown) to form the VAH. Generally, the steam contacts the AAH feedstream 104 prior to the AAH feedstream 104 entering the reaction vessel 102, but may be added to the system 100 in any manner known to one skilled in the art. Although the amount of steam contacting the AAH is determined by individual process parameters, the AAH feedstream 104 may have a steam to AAH weight of from about 0.01 to about 15:1, or from about 0.3:1 to about 10:1, or from about 0.6:1 to about 3:1, or from about 0.8:1 to about 2:1, for example.

One specific embodiment includes the conversion of ethylbenzene to styrene, where the VAH exit stream 108 may include styrene, toluene, benzene, and/or unreacted ethylbenzene, for example. In other embodiments, the process includes the conversion of ethyltoluene to vinyltoluene, cumene to alpha-methylstyrene and/or normal butylenes to butadiene, for example.

The dehydrogenation processes discussed herein are high temperature processes. As used herein, the term "high temperature" refers to process operation temperatures, such as reaction vessel and/or process line temperatures (e.g., the temperature of the feedstream at the vessel inlet) of from about 150° C. to about 1000° C., or from about 300° C. to about 800° C., or from about 500° C. to about 700° C., or from about 550° C. to about 650° C., for example.

A variety of catalysts can be used in the catalytic dehydrogenation system 100. A representative discussion of some of those catalysts (e.g., dehydrogenation catalysts) is included below, but is in no way limiting the catalysts that can be used in the embodiments described herein.

The dehydrogenation catalysts discussed herein generally include an iron compound and at least one alkali metal compound. For example, the dehydrogenation catalyst may include from about 40 weight percent to about 90 weight percent iron, or from about 70 wt. % to about 90 wt. % iron, or from about 80 wt. % to about 90 wt. % iron. The iron compound can be iron oxide, or another iron compound known to one skilled in the art.

Further, the dehydrogenation catalyst may include from about 5 weight percent to about 60 weight percent alkali metal compound, or from about 8 wt. % to about 30 wt. % alkali metal compound, for example. The alkali metal compound may be potassium oxide, potassium hydroxide, potassium acetate, potassium carbonate or another alkali metal compound known to one skilled in the art, for example.

Additionally, the dehydrogenation catalysts may further include additional catalysis promoters (e.g., up to about 20 wt. % measured as their oxides, or from about 1 wt. % to about 4 wt. %), such as nonoxidation catalytic compounds of Groups IA, IB, IIA, IIB, IIIA, VB, VIB, VIIB and VIII and rare earth metals, such as zinc oxide, magnesium oxide, chromium or copper salts, potassium oxide, potassium carbonate, oxides of chromium, manganese, aluminum, vanadium, magnesium, thorium and/or molybdenum, for example.

Such dehydrogenation catalysts are well known in the art and some of those that are available commercially include: the S6-20, S6-21 and S6-30 series from BASF Corporation; the C-105, C-015, C-025, C-035, and the FLEXICAT series from CRI Catalyst Company, L.P.; and the G-64, G-84 and STYROMAX series from Sud Chemie, Inc. Dehydrogenation catalysts are further described in U.S. Pat. Nos. 5,503, 163 (Chu); 5,689,023 (Hamilton, Jr.) and 6,184,174 (Rubini, et al.), which are incorporated by reference herein.

The dehydrogenation catalyst may be loaded into any reaction vessel 102 known to one skilled in the art for the conversion of an AAH to a VAH. For example, the reaction vessel 102 may be a fixed bed vessel, a fluidized bed vessel and/or a tubular reactor.

Figure 2:
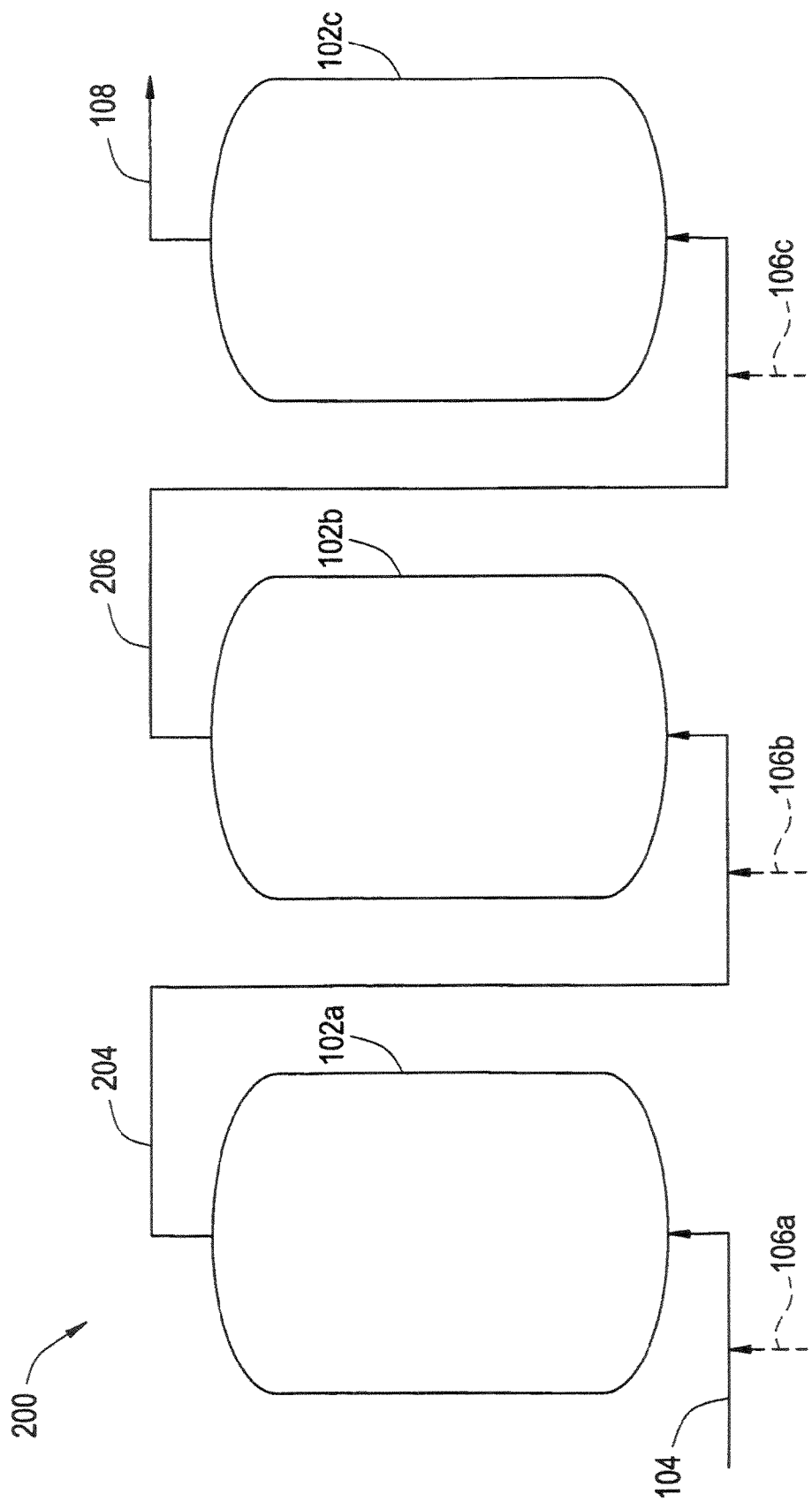
FIG. 2 illustrates a multistage catalytic dehydrogenation system.

Although a single stage process is shown in FIG. 1, multistage processes are often utilized to form vinyl aromatic hydrocarbons and an example of such (three stages 200) is shown in FIG. 2. Although FIG. 2 illustrates three reactors/stages, any number or combination of reactors may be utilized. In a multistage process, such as process 200, the exit stream (204, 206) of one reaction vessel (102A, 102B) becomes the feedstream (204, 206) to another reaction vessel (102B, 102C). Therefore, when the dehydrogenation process is a multistage process, the term "feedstream" as used herein, may be the exit stream from a previous reactor, a "fresh" feedstream and/or a recycled stream, for example. In such embodiments, the feedstream (e.g., 204, 206) may include steam, partially reacted alkyl aromatic hydrocarbon, unreacted alkyl aromatic hydrocarbon and/or vinyl aromatic hydrocarbon, for example. Further, it is known in the art that additional process equipment, such as reheaters (not shown) may be included to maintain and/or restore process stream temperatures within a desired range, such as within a high temperature range at a reaction vessel inlet.

One process for preparing vinyl aromatic hydrocarbons is the "Dow Process", which supplies superheated steam (720° C.) to a vertically mounted fixed bed catalytic reactor. The steam is generally injected into the reactor in the presence of a vaporized feedstream. See, The Chemical Engineers Resource Page at www.cheresources.com/polystymonzz.shtml.

Catalyst Life Extruder

During such dehydrogenation processes, it is desirable to maintain both high levels of conversion and high levels of selectivity. Unfortunately, catalysts tend to lose activity when exposed to reaction environments, thereby reducing the level of conversion and/or the level of selectivity. Such losses may result in an undesirable loss of process efficiency. Various methods for catalyst regeneration exist, but such methods generally involve stopping the reaction process and in some cases, removing the catalyst for external regeneration, resulting in increased costs, such as costs related to heat loss and lost production.

One method for overcoming the loss of catalyst activity includes raising the temperature of the feedstream and/or the reaction vessel. Such temperature increases raise the rate of reaction in order to offset the continuing loss of catalyst activity. The embodiments described herein contemplate such temperature increases in combination with other processes for catalyst regeneration. Unfortunately, above a certain temperature, the mechanical temperature limit of the process equipment or the dehydrogenation catalyst may be reached, thereby increasing the potential degradation of the catalyst physical structure and/or the integrity of the process equipment.

Returning to FIG. 1, one regeneration method that is described further below includes the addition of a catalyst life extender (CLE) 106 to the dehydrogenation process 100. The CLE 106 may be added to the system 100 at various points, including the reaction vessel 102, the catalyst bed (not shown) and/or process stream 104, for example. Such processes may avoid/delay the need for catalyst removal from the reaction vessel 102 for regeneration and/or disposal.

The catalyst life extender 106 may be selected from non-halogen sources of alkali metal ions and may include a combination thereof. The amount of catalyst life extender 106 added to the process depends at least in part on the reaction conditions, equipment, feedstream composition and/or the catalyst life extender 106 being used, for example.

Unfortunately, such an addition method may result in costly addition methods, such as the vaporization of molten potassium in order to eliminate and/or reduce fouling. For example, in the initial phases of industry implementation, aqueous potassium hydroxide (KOH) addition was attempted. It was determined that KOH addition, with the KOH being at ambient temperature, resulted in severe reactor fouling and plugging of the injection hardware and/or process line. Therefore, such catalyst life extenders are generally preheated to a temperature similar to that of the feedstream prior to addition.

However, in one embodiment, the catalyst life extender 106 is a compound containing potassium, is neither excessively deliquescent nor dangerously reactive and has a melting point or vapor point such that it can be used at dehydrogenation process temperatures without blocking process lines or fouling process equipment. For example, the catalyst life extender 106 may be a potassium salt of a carboxylic acid, such as potassium acetate.

Unexpectedly, it has been found that such catalyst life extenders (in aqueous form) are capable of being injected into high temperature process lines without the expected plugging/fouling. Rather, aqueous addition of the carboxylic acids described above resulted in markedly decreased fouling and in some instances, no fouling for extended periods of time. Previous attempts at aqueous potassium hydroxide addition resulted in plugging/fouling after only a short period of time, such as days, versus weeks or months.

Further, the catalyst life extender 106 is generally substantially free of any catalysts poisons. For example, it has been reported that halogen ions, such as chloride, may poison dehydrogenation catalysts. Therefore, the catalyst life extender 106 includes little or no halogen substituents.

The catalyst life extender 106 may be supplied to the system 100 at a rate equivalent to a continuous addition of from about 0.01 to about 100 parts per million by weight of catalyst life extender relative to the weight of the total alkyl aromatic hydrocarbon in the feedstream 104, or from about 0.10 to about 10 parts per million, for example.

Just as the catalysts life extenders can be introduced into the dehydrogenation process by more that one method, it is also within the scope of the present invention to introduce the catalyst life extenders 106 to the dehydrogenation process at more than one rate. For example, the catalyst life extenders 106 can be introduced continuously or periodically, such as when catalyst activity levels fall below a predetermined level. In still another embodiment, the catalyst life extenders may be added at a relatively low level with additional catalyst life extender being added to the process when catalyst activity levels fall below a predetermined level. Accordingly, the system may include monitoring means (not shown) to monitor temperatures and chemical compositions to determine when conversion drops below a predetermined level.

Prior to the embodiments described herein, aqueous addition methods have been unsuccessful, at least in part because the feedstream 104 is usually passing at a very high velocity, such as 20 ft/s, or from about 10 ft/s to about 30 ft/s, or from about 15 ft/s to about 25 ft/s, or at a velocity of about 15 ft/s or more, for example, through a large diameter conduit, such as 54 inches to 60 inches.

Surprisingly, the embodiments described herein are capable of adding catalyst life extenders to high temperature process streams while exhibiting minimal fouling/plugging of the either the reactors or process lines.

Although described herein in terms of catalytic dehydrogenation processes, the embodiments described herein may be used for aqueous salt addition into any high temperature conversion process, including the formation of gasoline fraction hydrocarbons from syntheses gas, dealkylation of alkylaromatics (e.g., toluene to benzene) and syntheses of ammonia from nitrogen and hydrogen. Generally, when referring to high temperature processes, the aqueous salt is added to a process stream having such high temperature.

EXAMPLE

Example 1

A steam and ethylbenzene feedstream was contacted with a potassium promoted iron oxide dehydrogenation catalyst in a reaction to form styrene. The feedstream (10:1 molar ratio of steam:ethylbenzene) was fed to the reaction via a first conduit (54 inch diameter) at a temperature of about 1200° F. (649° C.) and a velocity of about 20 ft/s. Prior to the reactor inlet, aqueous potassium acetate was injected into the first conduit to contact and mix with the feed stream. The potassium acetate was at ambient temperature prior to injection Two months after startup of the above process, a gamma scan of the conduit and the reactor observed essentially no deposits therein.

Example 2

An apparatus was constructed to investigate the vaporization of potassium salt solutions intended for injection into styrene catalytic reactors during operation. The initial design consisted of a salt solution line and a carrier steam line connected to a mixer in a box furnace. Downstream from the mixer was an alumina bed intended to trap the vaporized potassium salt. The carrier steam line used a peristaltic pump for a water flow of 0.4 ml/min pumped into a 350° C. furnace through ⅛" tubing with a supplemental addition of 30 mL/min of nitrogen. After the carrier steam was detected at the knockout pot, various potassium salt solutions were pumped in at 0.25 ml/min through ¹⁄₁₆" tubing using a peristaltic pump. This salt solution line was insulted by jacketing with a ¼" tube and a nitrogen purge to keep the solution from vaporizing prematurely inside the furnace. The potassium salt solution entered a mixing chamber vertically and was swept into a trapping bed of aluminum oxide by the steam/nitrogen. Evaluations were run for 6 hours. The water collected in a knockout pot and the alumina bed was analyzed for potassium deposition.

The first potassium salt solution analyzed was a 0.1 M potassium acetate solution. After running for 6 hours, the alumina bed was cooled and dried under nitrogen. Inductively Coupled Plasma (ICP) analysis was performed and showed that there was 1032 ppm of potassium on the alumina after potassium salt addition. The reference sample included 1151 ppm of potassium. A second reference sample was analyzed separately from any K-containing samples and 617 ppm potassium was observed. A third reference was then analyzed and 464 ppm potassium was observed in the aluminum oxide.

A 0.1 M potassium acetate solution was analyzed using the same flow rates as above but an oven temperature of 400° C. and 1022 ppm potassium was observed in the alumina bed. A second run of the 0.1 M potassium acetate was conducted at 400° C. and 1200 ppm potassium was observed in the alumina bed.

A 0.1 M potassium citrate solution was evaluated with a furnace temperature of 350° C. and the salt was deposited in the mixing chamber and plugged up the inlet to the alumina bed but 1908 ppm were trapped in the alumina bed. A 0.1 M potassium citrate solution was evaluated at 400° C. and 1472 ppm potassium were deposited in the alumina bed but the mixing chamber and the lines remained clean at this higher temperature. A second run of 0.1 M potassium citrate was conducted at 400° C. and 975 ppm potassium was deposited in the alumina bed. The mixing chamber and lines remained clean once again at this higher temperature.

A 0.1 M potassium benzoate solution was analyzed using the same procedure as the previous salts and an ICP of the alumina bed showed 1006 ppm potassium present. The salt plugged up the 1/16" tubing line and left a white coating in the mixing chamber. Irregularities were suspected.

A 0.1 M potassium benzoate solution was analyzed at 400° C. and 1171 ppm potassium were deposited in the alumina bed. The lines did not foul at the higher oven temperature. A second run of 0.1 M potassium benzoate was performed at 400° C. and 1395 ppm potassium were deposited in the alumina bed. The mixing chamber and lines remained clean once more at this higher temperature.

The runs using the various salts at 0.1 M were successful at 400° C. so they were repeated at 0.4 M to see if the increase in potassium would foul the lines. The medium used to trap the potassium was changed to Selexsorb and reference samples were analyzed by ICP and showed 1400 ppm potassium present.

A 0.4 M potassium acetate solution was analyzed at 400° C. using the same flow rates as above and 2076 ppm potassium were deposited in the alumina trap without fouling the lines.

A 0.4 M potassium citrate solution was analyzed at 400° C. using the same flow rates as above and 2370 ppm potassium were found in the alumina trap without fouling the lines. A second run of the 0.4 M potassium citrate was conducted and 2161 ppm potassium were deposited in the lines. After this run, the salt line had deposits and the alumina had a dark brown coating. The inlet to the mixing chamber was also caked in a black residue.

A 0.4 M potassium benzoate solution was analyzed at 400° C. using the same flow rates as above and 1939 ppm potassium were found in the alumina trap without fouling the lines.

After the successful runs at 0.4 M potassium salt solutions, two runs were conducted using 0.1 M potassium carbonate and the lines were fouled after only about 20 mL of the potassium carbonate solution had been pumped through. Even though these runs were brief, the alumina was analyzed and found 3549 and 3715 ppm potassium from the two potassium carbonate runs.

While the foregoing is directed to embodiments of the present invention, other and further embodiments of the invention may be devised without departing from the basic scope thereof and the scope thereof is determined by the claims that follow.

What is claimed is:

1. A method for preparing a vinyl aromatic hydrocarbon comprising:
    providing a feed stream comprising an alkyl aromatic hydrocarbon and steam;
    contacting the feed stream with a dehydrogenation catalyst to form a vinyl aromatic hydrocarbon, the dehydrogenation catalyst comprising iron oxide and a potassium catalysis promoter; and
    supplying a catalyst life extender to at least one reaction chamber, the reaction chamber loaded with the dehydrogenation catalyst, wherein the catalyst life extender comprises a potassium salt of a carboxylic acid which is selected from the group consisting of potassium acetate, potassium citrate, potassium benzoate and combinations thereof and is supplied to the reaction chamber in aqueous form.

2. The method of claim 1 further comprising supplying the catalyst life extender to the at least one reaction chamber at a rate equivalent to a continuous addition of from about 0.01 to about 100 parts per million by weight of catalyst life extender relative to the weight of the total alkyl aromatic hydrocarbon directed into the reaction chamber.

3. The method of claim 1 further comprising supplying the catalyst life extender to the at least one reaction chamber at a rate equivalent to a continuous addition of from about 0.10 to about 10 parts per million by weight of catalyst life extender relative to the weight of the total alkyl aromatic hydrocarbon directed into the reaction chamber.

4. The method of claim 1 further comprising supplying the catalyst life extender to the reaction chamber without interrupting the formation of the vinyl aromatic hydrocarbon.

5. The method of claim 1, wherein the alkyl aromatic hydrocarbon comprises ethylbenzene and the vinyl aromatic hydrocarbon comprises styrene.

6. The method of claim 1, wherein the catalyst life extender comprises potassium acetate.

7. The method of claim 1, wherein the catalyst life extender comprises a potassium salt of a carboxylic acid comprising from 2 to 10 carbon atoms.

8. The method of claim 1 further comprising supplying the catalyst life extender to the reaction chamber without preheating.

* * * * *